United States Patent [19]

Bittler et al.

[11] Patent Number: 5,010,071
[45] Date of Patent: Apr. 23, 1991

[54] ANDROSTANE DERIVATIVES

[75] Inventors: Dieter Bittler; Henry Laurent; Petra Rach; Michael Topert, all of Berlin, Fed. Rep. of Germany

[73] Assignee: Schering Aktiengesellschaft, Berlin and Bergkamen, Fed. Rep. of Germany

[21] Appl. No.: 379,399

[22] Filed: Jul. 13, 1989

[30] Foreign Application Priority Data

Jul. 13, 1988 [DE] Fed. Rep. of Germany ....... 3824247

[51] Int. Cl.$^5$ .......................... A61K 31/56; C07J 1/00
[52] U.S. Cl. .................... 514/178; 514/177; 514/859; 514/864; 552/634; 552/635
[58] Field of Search ............... 514/177, 178, 859, 864; 552/634, 635

[56] References Cited

U.S. PATENT DOCUMENTS

| | | | |
|---|---|---|---|
| 4,344,941 | 8/1982 | Wiechert et al. | 514/178 |
| 4,456,600 | 6/1984 | Weichert et al. | 514/178 |
| 4,457,925 | 7/1984 | Bittler et al. | 514/178 |
| 4,558,041 | 12/1985 | Weichert et al. | 514/178 |

Primary Examiner—Stanley J. Friedman
Assistant Examiner—Kevin Weddington
Attorney, Agent, or Firm—Millen, White & Zelano

[57] ABSTRACT

Androstane derivatives of the general Formula I

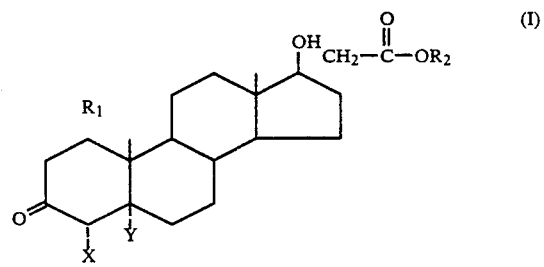

in which
 $R_1$ represents a hydrogen atom or a methyl group,
 X and Y each mean hydrogen atoms or together a carbon-carbon bond, and
 $R_2$ symbolizes a hydrogen atom or an alkyl group with 1 to 6 carbon atoms, are pharmaceutically effective substances which have a distinct antiandrogenic effectiveness in topical application.

17 Claims, No Drawings

ANDROSTANE DERIVATIVES

SUMMARY OF THE INVENTION

The invention relates to new androstane derivatives of general Formula I

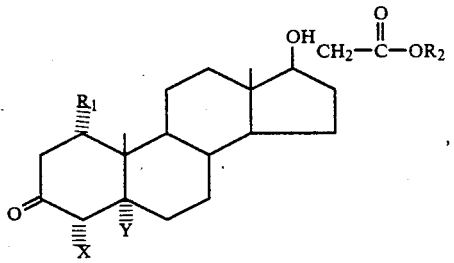

in which
R₁ represents a hydrogen atom or a methyl group,
X and Y mean each mean hydrogen atoms or together a carbon-carbon bond and
R₂ symbolizes a hydrogen atom or an alkyl group with 1 to 6 carbon atoms and pharmaceutical preparations which contain one or two of these androstane derivatives as an active ingredient.

By an alkyl radical R₂, a straight-chain or branched saturated alicyclic hydrocarbon radical with 1 to 6 carbon atoms is meant. As suitable alkyl radicals there can be mentioned, for example: the methyl radical, the ethyl radical, the propyl radical, the isopropyl radical, the butyl radical, the 2-butyl radical, the 2-methylpropyl radical, the tert.-butyl radical, the pentyl radical or the hexyl radical.

In addition the invention relates to a process for the production of androstane derivatives of general formula Ia

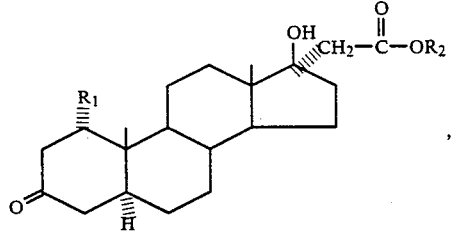

in which R₁ and R₂ have the above mentioned meaning, wherein a steroid ketal of general formula II, in which R₁ and R₂ have the above-mentioned meaning and Z represents an alkylene group with 1 to 6 carbon atoms, is hydrolytically cleaved,

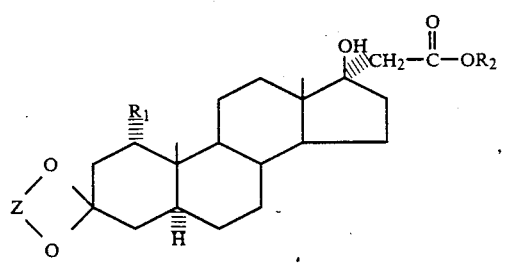

and optionally the 17alpha-alkoxycarbonyl compounds of general formula Ia are saponified and/or the carboxylic acids of general formula Ia are esterified.

Finally the invention relates to a process for the production of androstane derivatives of general formula Ib

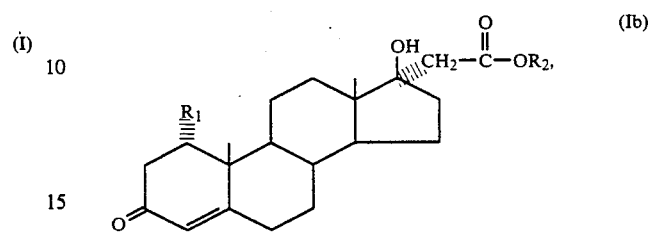

in which R₁ and R₂ have the above-mentioned meaning, wherein an enol ether of general formula III

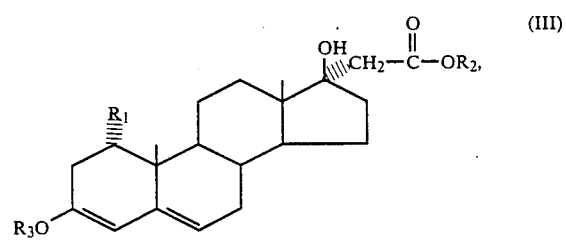

in which R₁ and R₂ have the above mentioned meaning and R₃ represents an alkyl group with 1 to 6 carbon atoms or a ketal of general formula IV

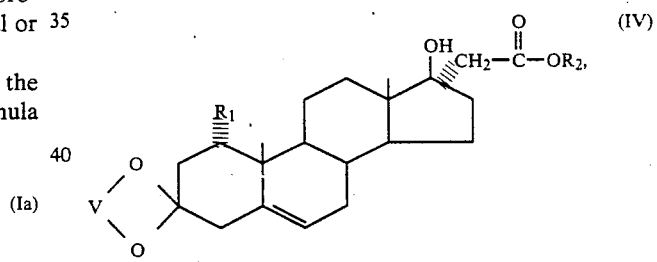

in which R₁ and R₂ have the above mentioned meaning and V represents an alkylene group with 1 to 6 carbon atoms, is hydrolytically cleaved and optionally the 17alpha-alkoxycarbonyl compounds of general formula Ib are saponified and/or the carboxylic acids of general formula Ib are esterified.

The performance of the process according to the invention takes place under conditions well known to one skilled in the art. Thus, for example, the cleavage of the ketals and enol ethers can be performed under the conditions described in the book by Carl Djerassi "Steroid Reactions"; Holden-Day Inc.; San Francisco 1963. The saponification of the alkoxycarbonyl compounds and esterification of the carboxylic acids can be performed, for example, under the conditions described in U.S. Pat. No. 3,824,260.

The initial compounds for the process according to the invention can be produced from the corresponding 17-keto compounds, by the latter being alkylated with bromoacetic acid alkyl esters, for example, under the conditions, as mentioned in the embodiments below.

The compounds of general formula Ia and those of general formula Ib (of which, however up to now, only such compounds have been examined in greater detail which carry a hydrogen atom as $R_1$ substituent) show a distinct antiandrogenic effectiveness in topical application, and in systemic application are only slightly effective, which is desirable in topical applications.

The pharmacologically active compounds of this invention can be processed in accordance with conventional methods of galenic pharmacy to produce compositions for administration to patients, e.g., mammals including humans. Conventional excipients are pharmaceutically acceptable organic or inorganic carrier substances suitable for topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides pentaerythritol fatty acid esters, hydroxymethylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring, and/or aromatic substances and the like which do not deleteriously react with the active compounds.

Dosages for a given host can be determined using conventional considerations, e.g., by customary comparison of the differential activities of the subject compound and of a known agent, e.g., by means of an appropriate, conventional pharmacological protocol.

Preferably, the compounds are formulated for topical use. For such topical use, the compounds according to the invention can be processed with the usual vehicles into solutions, gels, ointments, powders, or other preparations. Suitable vehicles are, for example, water, ethanol, propanol, glycerin, methylcellulose, hydroxypropylcellulose, carboxymethylene, etc. The antiandrogen is preferably present in a concentration of 0.05 to 5.0% by weight, related to the total weight of the preparation. The preparations may be used for treatment of diseases like acne, seborrhea, alopecia, and hirsutism.

In particular, the compounds of the invention are effective in treating androgen-dependent diseases, e.g., as antiandrogens. Antiandrogenic effectiveness of the compounds may be determined as set forth in U.S. Pat. No. 4,344,941.

The embodiments below serve to explain in greater detail the process according to the invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire texts of all applications, patents and publications, if any, cited above and below, and of corresponding West German Application No. P 38 24 247.8, filed July 13, 1988, are hereby incorporated by reference.

EXAMPLES

EXAMPLE 1

(a) A solution of 450 mg copper (II)-acetate is mixed in 111 ml of ethylene glycol dimethyl ether is mixed with 22.5 g of zinc dust and 2.15 ml of acetic acid and stirred at room temperature until decoloration of the solution. To the reaction mixture 0.75 ml of triethylamine and 15 g of 3.3-ethylenedioxy-1alpha-methyl-5alpha-androstan-17-one (produced according to EP-A No. 71153) are added and within 90 minutes 50.25 ml of ethyl bromoacetate is instilled. Then it is stirred for 2 hours at room temperature and the excess reagent is decomposed with saturated ammonium chloride solution. After addition of diethyl ether, the aqueous phase is separated and the organic phase is washed with ammonium chloride solution and water. After drying and concentration by evaporation, the residue is chromatographed on silica gel and 12.5 g of 3.3 ethylenedioxy-17alpha-ethoxycarbonylmethyl-1alpha-methyl-5alpha-androstan-17beta-ol is obtained.

(b) A solution of 4.2 g of 3.3-ethylenedioxy-17alpha-ethoxycarbonylmethyl-1alpha-methyl-5alpha-androstan-17beta-ol in 42 ml of methanol and 21 ml of tetrahydrofuran is mixed with 4.2 ml of 8% sulfuric acid and allowed to stand for 90 min. at room temperature. The reaction mixture is diluted with diethyl ether, washed neutral with water, dried and concentrated by evaporation. The residue is chromatographed on silica gel. 3.2 g of 17alpha-ethoxycarbonylmethyl-17beta-hydroxy-1alpha-methyl-5alpha-androstan-3-one is isolated as viscous oil.

EXAMPLE 2

A solution of 3.9 g of 17alpha-ethoxycarbonylmethyl-17beta-hydroxy-1alpha-methyl-5alpha-androstan-3-one in 88 ml of methanol and 58 ml of water is mixed with 9.7 ml of 2N sodium hydroxide solution and is stirred 2.5 hours at room temperature. The reaction solution is diluted with water, extracted twice with diethyl ether and acidified with 12 ml of 2N sulfuric acid. The released carboxylic acid is taken up in dichloromethane, the organic phase is washed with water, dried and concentrated by evaporation. 3.3 g of 17alpha-carboxymethyl-17beta-hydroxy-1alpha-methyl-5-alpha-androstan-3-one is obtained as an oily product.

EXAMPLE 3

An ice-cooled solution of 700 mg of 17alpha-carboxymethyl-17beta-hydroxy-1alpha-methyl-5alpha-androstan-3-one in 15 ml of tetrahydrofuran is mixed with 10 ml of an ethereal diazomethane solution (produced from 700 mg of nitrosomethyl urea) and allowed to stand for 30 min. with ice cooling. The solution is evaporated to dryness in a vacuum and the residue is chromatographed on silica gel. After recrystallization from diisopropyl ether 340 mg of 17beta-hydroxy-17alpha-methoxycarbonylmethyl-1alpha-methyl-5alpha-androstan-3-one with the melting point of 119.5° C. is obtained.

EXAMPLE 4

A solution of 750 mg of 17alpha-carboxymethyl-17beta-hydroxy-1alpha-methyl-5alpha-androstan-3-one in 7.5 ml of dimethylformamide is stirred for 1.5 hours at 60° C. after addition of 0.52 ml of 1-bromopropane and 520 mg of silver oxide. Then it is diluted with diethyl ether, washed with water, dried and concentrated by evaporation. The residue is chromatographed on silica gel, and 710 mg of 17beta-hydroxy-1alpha-methyl-17alpha-propoxycarbonylmethyl-5alpha-androstan-3-one is obtained as oil.

EXAMPLE 5

A solution of 630 mg of 17alpha-carboxymethyl-17beta-hydroxy-1alpha-methyl-5alpha-androstan-3-one in 5.8 ml of dimethylformamide is mixed with 0.488 ml of 1-bromobutane and 438 mg of silver oxide and stirred 1.5 hours at 60° C. It is worked up and chromatographed, as described in Example 4. 430 mg of oily 17alpha-butoxycarbonylmethyl-17beta-hydroxy-1alpha-methyl-5alpha-androstan-3-one is obtained.

EXAMPLE 6

10 g of 3-methoxy-3.5-androstadien-17-one (produced according to J. Org. Chem. 26 (1961) 3925) is reacted and worked up, as described in Example 1, in ethylene glycolmethyl ether with zinc-copper and ethyl bromoacetate. After chromatogry on silica gel 9 g of 17alpha-ethoxycarbonylmethyl-17beta-hydroxy-3-methoxy-3.5-androstadiene containing ethyl bromoacetate is obtained, which is dissolved in 90 ml of methanol and 45 ml of tetrahydrofuran. The solution is allowed to stand at room temperature after addition of 9 ml of 8% sulfuric acid, is diluted with diethyl ether and washed neutral with water and dried. The solvent is evaporated in a vacuum and the residue is chromatographed on silica gel. After recrystallization from diisopropyl ether 1.6 g of 17alpha-ethoxycarbonylmethyl-17beta-hydroxy-4-androstan-3-one the melting point of 88° C. is obtained.

EXAMPLE 7

A solution of 1.1 g of 17alpha-ethoxycarbonylmethyl-17beta-hydroxy-4-androstan-3-one in 30 ml of methanol and 16.3 ml of water is mixed with 3.73 ml of 2N sodium hydroxide solution and allowed to stand 2 hours at room temperature. The reaction solution is diluted with water, extracted twice with diethyl ether and acidified with 4.5 ml of 2N sulfuric acid. The resulting carboxylic acid is taken up with dichloromethane, the organic phase is washed with water, dried and concentrated by evaporation. 920 mg of 17alpha-carboxymethyl-17beta-hydroxy-4-androstan-3-one is obtained as raw product.

EXAMPLE 8

400 mg of 17alpha-carboxymethyl-17beta-hydroxy-4-androstan-3-one is reacted and worked up with ethereal diazomethane solution in tetrahydrofuran as described in example 3. After chromatography and crystallization from diisopropyl ether 225 mg of 17beta-hydroxy-17alpha-methoxycarbonylmethyl-4-androstan-3-one with the melting point of 114° C. is obtained.

EXAMPLE 9

300 mg of 17alpha-carboxymethyl-17beta-hydroxy-4-androstan-3-one is reacted and worked up with silver oxide and 1-bromopropane, as described in Example 4. After chromatography on silica gel 180 mg of 17beta-hydroxy-17alpha-propoxycarbonylmethyl-4-androstan-3-one with the melting point of 130° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An androstane derivative of the formula

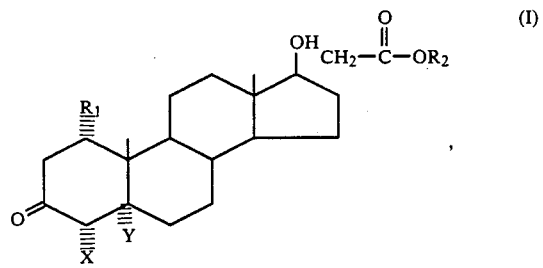

wherein
$R_1$ is hydrogen or methyl,
X and Y are each hydrogen and
$R_2$ is hydrogen or $C_{1-6}$-alkyl.

2. 17α-ethoxycarbonylmethyl-17β-hydroxy-1α-methyl-5α-androstan-3-one, a compound of claim 1.
3. 17α-carboxymethyl-17β-hydroxy-1α-methyl-5α-androstan-3-one, a compound of claim 1.
4. 17β-hydroxy-17α-methoxycarbonylmethyl-1α-methyl-5α-androstan-3-one, a compound of claim 1.
5. 17β-hydroxy-1α-methyl-17α-propoxycarbonylmethyl-5α-androstan-3-one, a compound of claim 1.
6. 17α-butoxycarbonylmethyl-17β-hydroxy-1α-methyl-5α-androstan-3-one, a compound of claim 1.
7. 17α-ethoxycarbonylmethyl-17β-hydroxy-4-androstan-3-one, a compound of claim 1.
8. 17α-carboxymethyl-17β-hydroxy-4-androstan-3-one, a compound of claim 1.
9. 17β-hydroxy-17α-methoxycarbonylmethyl-4-androstan-3-one, a compound of claim 1.
10. 17β-hydroxy-17α-propoxycarbonylmethyl-4-androstan-3-one, a compound of claim 1.
11. A compound of claim 1, of the formula

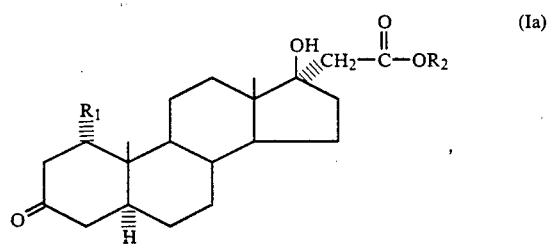

12. A pharmaceutical composition comprising a pharmaceutically acceptable carrier and at least one compound of claim 1.
13. A composition according to claim 12, wherein the carrier is a topical carrier.
14. A method for the treatment of acne, comprising administering a pharmaceutically effective amount of a compound of claim 1.
15. A method for the treatment of seborrhea, comprising administering a pharmaceutically effective amount of a compound of claim 1.
16. A method for the treatment of alopecia, comprising administering a pharmaceutically effective amount of a compound of claim 1.
17. A method for the treatment of hirsutism, comprising administering a pharmaceutically effective amount of a compound of claim 1.

* * * * *